United States Patent [19]

Takahashi et al.

[11] Patent Number: 5,099,076
[45] Date of Patent: Mar. 24, 1992

[54] METHOD FOR PREPARING P,P'-BIPHENOL

[75] Inventors: Katsunori Takahashi; Mikio Kawahara; Shunji Yago; Yoshiharu Ayabe, all of Wakayama, Japan

[73] Assignee: Honshu Chemical Industry Co., Ltd., Tokyo, Japan

[21] Appl. No.: 593,114

[22] Filed: Oct. 5, 1990

[30] Foreign Application Priority Data

Oct. 6, 1989 [JP] Japan .................. 64-259907

[51] Int. Cl.$^5$ ................ C07C 39/14; C07C 37/50; C07C 37/84
[52] U.S. Cl. .................. 568/730; 568/722; 568/730; 568/784; 568/789; 568/802; 568/805
[58] Field of Search ............ 568/730, 784, 805, 789, 568/802, 722, 989

[56] References Cited

U.S. PATENT DOCUMENTS

| | | | |
|---|---|---|---|
| 4,100,205 | 7/1978 | Rutledge | 568/730 |
| 4,560,809 | 12/1985 | Goins et al. | 568/784 |
| 4,891,453 | 1/1990 | Tanaka et al. | 568/830 |

FOREIGN PATENT DOCUMENTS

| | | | |
|---|---|---|---|
| 0035965 | 9/1981 | European Pat. Off. | 568/730 |
| 0309226 | 3/1989 | European Pat. Off. | 568/730 |
| 1268641 | 11/1986 | Japan | 568/730 |

Primary Examiner—Werren B. Lone
Attorney, Agent, or Firm—Felfe & Lynch

[57] ABSTRACT

The present invention is directed to a method for the preparation of p,p'-biphenol by simplified processes achieved by batch or continuous operations which comprises using phenol and isobutylene as starting materials, allowing phenol to react with isobutylene in the presence of aluminum phenoxide, oxidizing the resulting reaction liquid in the presence of an alkaline catalyst, and debutylating the reaction liquid in the presence of a debutylation catalyst.

5 Claims, 1 Drawing Sheet

METHOD FOR PREPARING P,P'-BIPHENOL

FIELD OF THE INVENTION

The present invention relates to a method for the preparation of p,p'-biphenol, which is a useful material for liquid crystal polymer, engineering plastics modifier, phenol resin modifier and super engineering plastics modifier, from phenol and isobutylene by means of a consistent and simplified processes with easy operations as well as with high efficency.

BACKGROUND OF THE INVENTION

As a conventional method for preparing p,p'-biphenol, a method is known which comprises using 2,6-di-t-butyl phenol (hereinafter referred to as 2,6B) as a chief raw material, allowing said material to be subjected to oxidative coupling in the presence of an alkaline catalyst to have 3,3',5,5'-tetra-t-butyl diphenoquinone produced followed by the reduction thereof with hydrogen to obtain 3,3',5,5'-tetra-t-butyl biphenol (hereinafter referred to as TBBP) and then debutylating the TBBP. See reference P.3.

As a method of debutylating TBBP, a method is disclosed in Japanese Patent Laid-open No. 1434/1984 to obtain p,p'-biphenol wherein TBBP isolated from an oxidation liquid is subjected to reaction by heating in the presence of phenol and activated clay for permitting the t-butyl group of TBBP to be transalkylated to the meta position of phenol.

In said method for preparing p,p'-biphenol, each of intermediates, 2,6B and TBBP is purified through isolation in the corresponding formation stage, and is used as the raw material for the following process. Each of the purification processes through isolation, therefore, necessitates its additional apparatus, and for the operation thereof some persons will be needed for process control and operations, in addition, resulting complicated operations will ineviably lead to decreased production efficiency.

SUMMARY OF THE INVENTION

It is an object of the present invention to provide consistent processes for preparing p,p'-biphenol, which are economical, employs simplified equipment and easy operations, from phenol and isobutylene as starting materials, and via no intermediate purification processes through isolation.

In other words, the present invention is to provide a method for obtaining p,p'-biphenol by means of consistently simplified processes with easy operations as well as with high efficency, wherein phenol is allowed to react with isobutylene in the presence of aluminum phenoxide to have 2,6B produced, the resulting reaction liquid is subjected to oxidation in the presence of an alkaline catalyst to have TBBP produced without the isolation of the 2,6B, and the oxidation reaction liquid is subsequently subjected to debutylation in the presence of a debutylation catalyst, and then crude crystals, obtained from the reaction liquid by cooling-crystallization, are purified.

References for the conventional method hereby incorporated by reference are U.S. Pat. No. 4,086,253, Japanese laid-open Nos. 58-140,034 (or 140,034/1983) and No. 60,23,338 (or 23,338/1985).

The laid-open Japanese patent 1434/1984 is also incorporated by reference.

Figure 1:
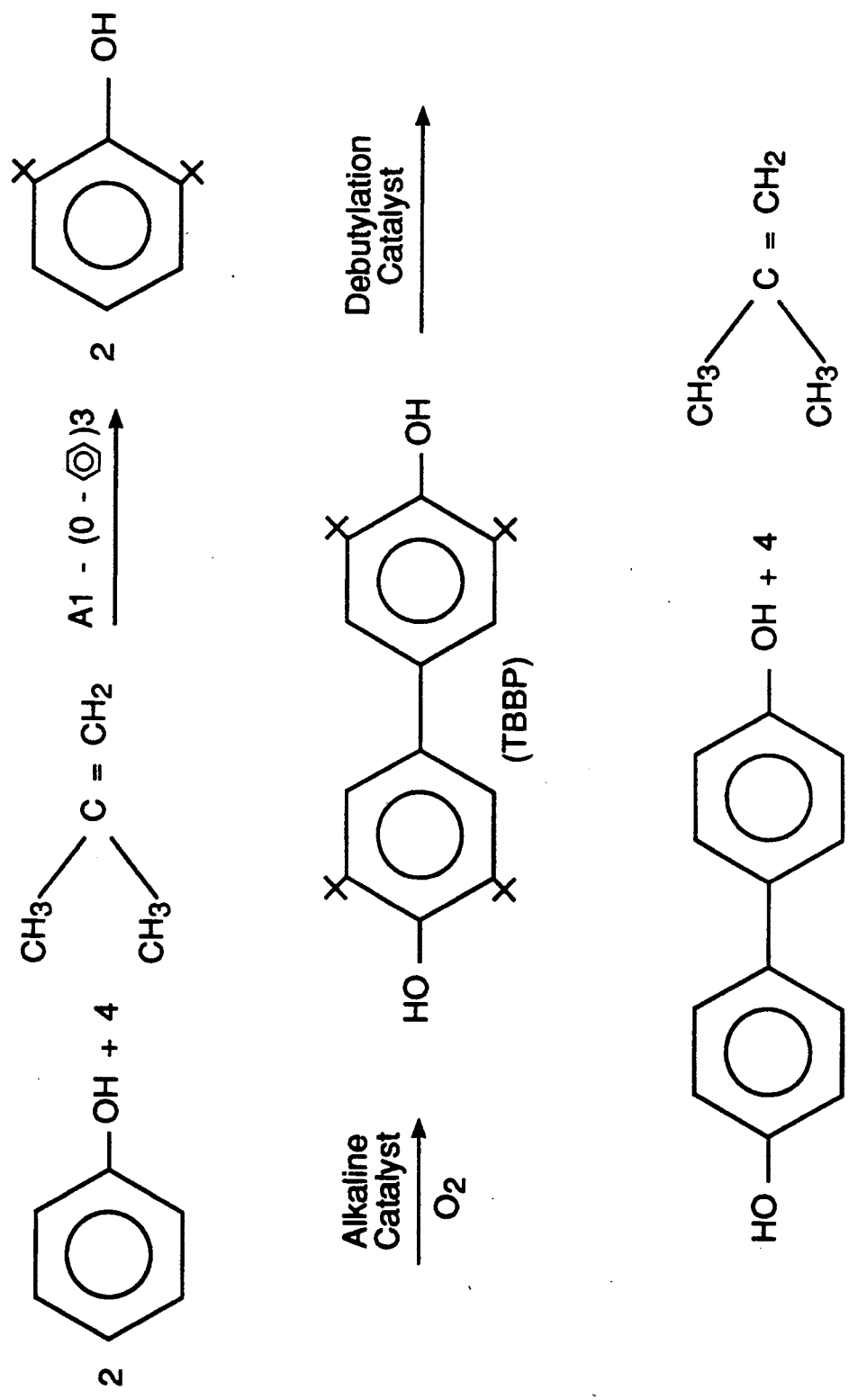
FIG. 1 shows a flow sheet of the reaction of the invention as described below.

Reaction 1. The first reaction shows phenol reacting with isobutylene to produce 2,6B.

Reaction 2. 2,6B subjected to oxidative coupling in the presence of an alkaline catalyst to produce TBBP.

Reaction 3. TBBP is debutylated in the presence of a debutylation catalyst to produce p,p'-biphenol.

DETAILED DESCRIPTION OF THE INVENTION

The first process in the present invention is a so-called butylation process wherein 2,6B is produced by allowing phenol to react with isobutylene using aluminum phenoxide as a catalyst.

In this process, into phenol are placed about 0.1 to 10% aluminum pieces preferably about 0.3 to 1% (relative to the weight of the penol), and when the mixture is heated up to about 150° C., there will be formed aluminum phenoxide with the generation of hydrogen gas. To the resulting liquid about 150 to 250 mol %, preferably about 190 to 220 mol % of isobutylene (relative to the amount of the phenol) is added gradually, and the butylation is carried out at a temperature of about 50° to 150° C. preferably at about 80° to 110° C. and a pressure of about 0 to 10 kg/cm$^2$ preferably about 1 to 3 kg/cm$^2$.

The reaction liquid obtained by said butylation process has a composition comprising not more than 10% phenol, not more than 30% 2-t-butyl phenol, not less than 50% 2,6B and not more than 50% 2,4,6-tri-t-butyl phenol, or comprising preferably not more than 5% phenol, not more than 15% 2-t-butyl phoenol, not less than 70% 2,6B and not more than 30% 2,4,6-tri-t-butyl phenol. In such case, when the amount of phenol is more than 10%, the resulting product of p,p'-biphenol will be slightly colored and when the amount of 2,6B is less than 70%, lowered productivity will be achieved (the % described in the present specification is expressed as % by weight).

The second process in the present invention is a so-called oxidation process wherein after the removal of the catalyst alone from said reaction liquid obtained by the first process, 0.1 to 10 wt. %, preferably 0.2 to 2.0 wt. % an alkaline catalyst such as potassium hydroxide, sodium hydroxide or the like is added to the resulting liquid, and then oxidized by the blowing of oxygen or a gas containing oxygen through the reaction liquid at a temperature of about 150 to 250 C. preferably at about 180 to 200 C. and at a pressure of about 0 to 50 kg/cm, preferably at about 0 to 5 kg/cm. Absorption amount of oxygen is about 10 to 30 mol %, preferably about 15 to 25 mol % (relative to the amount of 2,6B).

In the second process, 2,6B contained in the reaction liquid obtained by the first process is subjected to oxidative coupling to produce TBBP.

The third process in the present invention is a so-called debutylation process wherein to the reaction liquid containing TBBP obtained in the second process is added debutylation catalyst of which amount is the total of the amount required for neutralizing the alkaline used as an oxidative catalyst in the second process and the amount of 0.1 to 10 wt. %, preferably 0.5 to 5 wt. % relative to the amount of reaction liquid obtained in the second process. As for the debutylation catalyst in this process, p-toluene sulfonic acid (hereinafter referred to as PTSA), sulfuric acid, benzenesulfonic acid, aluminum phenoxides and aluminum alcoholates can be used. The debutylation is achieved at a temperature of about 100° to 250° C. preferably at about 130° to 220° C., and at a pressure of about 0 to 5 kg/cm preferably at normal pressures. Debutylation rate at the reaction end point is 90 to 95%.

The debutylation in the third process has the advantage that the butyl phenols such as 2-t-butyl phenol, 2,4,6-tri-t-butyl phenol, etc., which are contained in the oxidation reaction liquid of the second process, are used as solvents. These butyl phenols are also subjected to debutylation in the present process, and some of them are decomposed into isobutylene and phenol, however, most of them are decomposed to the extent that they change into p-t-butyl phenol, acting as a solvent.

Accordingly, the debutylation proceeds smoothly without the aid of any additional solvent.

The fourth process in the present reaction is a purification process to obtain pure p,p'-biphenol wherein the reaction liquid containing p,p'-biphenol obtained by said third process is cooled to crystallize crude p,p'-biphenol and followed by purification.

In the present fourth process, the reaction liquid obtained in the debutylation process is cooled at about 70° C., then crude p,p'-biphenol can be obtained. The resulting filtrate is recovered and circulated to the next time debutylation.

Thus obtained crude p,p'-biphenol is dissolved in a solvent such as methanol or the like and then subjected to purification by using activated carbon or the like, and there can be obtained a highly purified pure white product of p,p'-biphenol. The yield and purity thereof are 88 to 95 mol % (relative to the amount of TBBP) and 99.9% respectively.

Besides, each of the processes in the present invention can be conducted by either of continuous and batch operations, which can be optionally selected.

The present invention relates to a method of preparing highly pured p,p'-biphenol economically by simplified processes, wherein phenol and isobutylene are used as starting materials and no purification operations through isolation are employed during the consistent processes.

In the following, the present invention will be more concretely explained with reference to the examples of the present invention.

It will be understood that the specification and examples are illustrative but not limitative of the present invention and that other embodiments within the spirit and scope of the invention will suggest themselves to those skilled in the art.

EXAMPLE 1

Into 188 g (2 moles) phenol are placed 0.94 g aluminium pieces (0.5 wt % relative to the weight of the phenol), and when the mixture is heated up to 150° C., there will be formed aluminum phenoxide with the evolution of hydrogen. Into the resulting liquid isobutylene is forced under a pressure of 3 kg/cm$^2$ at 110° C. When isobutylene is absorbed as much as 246 g (4.4 mol %), the reaction is completed. The time required for the reaction is about 8 hours. This reaction liquid had a composition comprising 1.0% phenol, 4.1% 2-t-butyl phenol, 0.2% p-t-butyl phenol, 76% 2,6B, 1.1% 2,4,-di-t-butyl phenol and 17% 2,4,6-tri-t-butyl phenol (wherein % represnts % by weight). When 5.8 g (0.035 moles) of 24% sodium hydroxide is added to this solution and heated up to 200° C., a slurry of sodium aluminate is obtained. The sodium aluminate is separated from the liquid by filtration. To the filtrate is added 3.6 g (0.015 moles) of 24% potassium hydroxide, then air is blowed therethrough at 190° to 200° C. for 8 hours. Then 18.8 mol % oxygen was absorbed relative to the amount of 2,6B. After the completion of the reaction, the reaction liquid has a composition comprising 0.5% phenol, 3.8% 2-t-butyl phenol, 0.2% p-t-butyl phenol, 23% 2,6B, 1.2% 2,4,-di-t-butyl phenol, 17% 2,4,6-tri-t-butyl phenol, 0.3% 3,3',5,5'-tetra-t-butyl diphenoquinone and 54% TBBP (wherein % represents % by weight). And when 3.5 g PTSA is added to this reaction liquid and heated up to 220° C. for debutylation, 219 g isobutylene is recovered (recovery of the isobutylene is 89.0%) and 203 g slurry-like reaction liquid can be obtained. The liquid had a composition comprising 6.4% phenol, 0.1% 2-t-butyl phenol, 35% p-t-butyl phenol, 0.03% 2,6B, 4.5% 2,4,-di-t-butyl phenol, 0.02% 2,4,6-tri-t-butyl phenol, 51% p,p'-biphenol and 2.5% butyl biphenol (wherein % represents % by weight).

When this reaction liquid is cooled to 70° C. and filtrated, 96 g crude p,p'-biphnol can be obtained. The filtrate after the removal of the bipenol is distilled to recover butyl phenols and they are to be circulated for the next debutylation.

On the other hand, 96 g crude p,p'-biphenol is dissolved in 768 g methanol and the solution is treated with 1.9 g activated carbon (being 2 wt % based on the weight of the crude p,p'-biphenol), and after the recovery of methanol 76.8 g pure p,p'-biphenol can be obtained by filtration (yield by one-pass purification is 78%). The product had a purity of 99.9% and is pure white in color.

EXAMPLE 2

Into 188 g (2 moles) phenol placed 0.94 g aluminum pieces (0.5 wt % relative to the weight of the phenol), and when the mixture is heated up to 150° C., there will be produced aluminum phenoxide with the evolution of hydrogen. Into the resulting liquid isobutylene is forced under a pressure of 3 kg/cm at 110° C. When 207.2 g (3.7 mol %) isobutylene is absorbed, the reaction is completed. The time required for the reaction was about 8 hours. This reaction liquid has a composition comprising 1.2% phenol, 13.4% 2-t-butyl phenol, 0.25% p-t-butyl phenol, 73.5% 2,6B, 0.9% 2,4,-di-t-butyl phenol and 10.7% 2,4,6-tri-t-butyl phenol (wherein % represents % by weight). When 5.8 g (0.035 mole) of 24% sodium hydroxide is added to this solution and heated up to 200° C., a slurry of sodium aluminate is produced. The sodium aluminate is separated by filtration. To the filtrate is added 3.6 g (0.015 moles) of 24% potassium hydroxide, then air is blown therethrough at 190° to 200° C. for 8 hours. Then 19.7 mol % oxygen was absorbed relative to the amount of 2,6B. After the completion of the reaction, the resulting reaction liquid has a composition comprising 1.1% phenol, 13.3% 2-t-butyl phenol, 0.25% p-t-butyl phenol, 22.5% 2,6B, 0.9% 2,4,-di-t-butyl phenol, 10.9% 2,4,6-tri-t-butyl phenol, 0.4% 3,3',5,5'-tetra-t-butyl diphenoquinone and 50% TBBP (wherein % represents % by weight). And when 3.5 g PTSA is added to this reaction liquid and heated up to 220° C. for debutylation, 182 g isobutylene is recoverd (the recovery of the isobutylene is 87.8%) and 211 g slurry-like reaction liquid can be obtained. The liquid had a composition comprising 5.5% penol, 0.2% 2-t-butyl phenol, 42.2% p-t-butyl phenol, 0.05%

2,6B, 7.0% 2,4,-di-t-butyl phenol, 0.02% 2,4,6-tri-t-butyl phenol, 43% p,p'-biphenol and 1.5% butyl biphenol. When this reaction liquid is cooled to 70° C. and filtrated, 83 g crude p,p'-biphenol can be obtained. The filtrate after the removal of the bipenol by filtration is distilled to recover butyl phenols. And when they are circulated for the next debutylation, they will be further decomposed into iso butylene and phenol.

On the other hand, 83 g crude p,p'-biphenol is dissolved in 664 g methanol and the solution is treated with 1.7 g activated carbon (being 2 wt % based on the weight of the crude p,p'-biphenol) followed by hot-filtration, then the methanol is recovered from the resulting filtrate and followed by distillation and filtration, there can be obtained 65 g pure p,p'-biphenol (yield by one-pass purification is 78%). The product had a purity of 99.9% and is colored pure white.

What is claimed is:

1. A process for the preparation of p,p'-biphenol by batch or continuous operation which comprises
    allowing phenol to react with isobutylene in the presence of aluminum phenoxide to produce 2,6-di-t-butyl phenol,
    oxidizing the resulting reaction liquid using oxygen without isolating said 2,6-di-t-butyl phenol from the liquid in the presence of KOH or NaOH as an alkaline catalyst to produce 3,3',5,5'-tetra-t-butyl-4,4'-biphenol,
    subsequently debutylating the oxidation reaction liquid without any additional solvent in the presence of a debutylation catalyst selected from at least one of the group consisting of p-toluene sulfonic acid, sulphuric acid, benzenesulfonic acid, aluminum phenoxides and aluminum alcoholates, and
    then purifying crude crystals of 4,4'-biphenol so obtained by cooling-crystallization of the debutylation reaction liquid.

2. A process according to claim 1, wherein the reaction liquid obtained in the oxidation process has a composition comprising not more than 10% phenol, not more than 30% 2-t-butyl phenol, not less than 50% 2,6-di-t-butyl phenol and not more than 50% 2,4,6-tri-t-butyl phenol.

3. A process according to claim 1 wherein the oxidation is conducted by the blowing of oxygen or a gas containing oxygen through the reaction liquid in the presence of the alkaline catalyst at a temperature of about 150° to 250° C. and at a pressure of about 0 to 50 kg/cm$^2$.

4. A process according to claim 1 wherein the debutylation is conducted in the presence of a debutylation catalyst at a temperature of about 100° to 250° C. and at a pressure of about 0 to 5 kg/cm$^2$.

5. A process according to claim 1 wherein the purification is conducted by the treatment of crude crystals of p,p'-biphenol in a solvent using activated carbon.

* * * * *

UNITED STATES PATENT AND TRADEMARK OFFICE
CERTIFICATE OF CORRECTION

PATENT NO. : 5,099,076
DATED : March 24, 1992
INVENTOR(S) : Katsunori Takahashi, et al.

It is certified that error appears in the above-identified patent and that said Letters Patent is hereby corrected as shown below:

Col. 2, line 35:   change "phoenol" to -- phenol --.

Col. 3, line 67:   change "represnts" to -- represents --.

Col. 4, line 23:   change "biphnol" to -- biphenol --.

Signed and Sealed this

Fifth Day of October, 1993

*Attest:*

BRUCE LEHMAN

*Attesting Officer*   Commissioner of Patents and Trademarks